US010285657B2

(12) United States Patent
Ono et al.

(10) Patent No.: US 10,285,657 B2
(45) Date of Patent: May 14, 2019

(54) MEDICAL IMAGE DISPLAY PROCESSING METHOD, MEDICAL IMAGE DISPLAY PROCESSING DEVICE, AND PROGRAM

(71) Applicant: DAI NIPPON PRINTING CO., LTD., Tokyo (JP)

(72) Inventors: Tetsutaro Ono, Tokyo (JP); Tomoaki Goto, Ichikawa (JP); Hiroshi Matsuda, Tokorozawa (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 0 days.

(21) Appl. No.: 15/504,774

(22) PCT Filed: Sep. 24, 2015

(86) PCT No.: PCT/JP2015/076918
§ 371 (c)(1),
(2) Date: Feb. 17, 2017

(87) PCT Pub. No.: WO2016/047683
PCT Pub. Date: Mar. 31, 2016

(65) Prior Publication Data
US 2017/0273650 A1    Sep. 28, 2017

(30) Foreign Application Priority Data

Sep. 25, 2014  (JP) ................................ 2014-194786

(51) Int. Cl.
*A61B 6/00* (2006.01)
*G06F 19/00* (2018.01)
(Continued)

(52) U.S. Cl.
CPC .............. *A61B 6/501* (2013.01); *A61B 5/055* (2013.01); *G06F 19/00* (2013.01); *G06F 19/321* (2013.01);
(Continued)

(58) Field of Classification Search
None
See application file for complete search history.

(56) References Cited

U.S. PATENT DOCUMENTS 9,576,358 B2 *  2/2017  Kano ..................... A61B 5/055
2010/0016706 A1 *  1/2010  Wohlgemuth ......... A61B 5/055
600/410

FOREIGN PATENT DOCUMENTS

EP    2647335 A1   10/2013
EP    2 762 072 A1   8/2014
(Continued)

OTHER PUBLICATIONS

Wen et al. (2006) "Gray matter reduction is correlated with white matter hyperintensity volume: A voxel-based morphometric study in a large epidemiological sample," NeuroImage, vol. 29, pp. 1031-1039.*

(Continued)

*Primary Examiner* — Soo Shin
(74) *Attorney, Agent, or Firm* — Oliff PLC (57) ABSTRACT

A diagnosis support device, which is suitable for comparing different diseases, is provided, along with others. In the diagnosis support device, the input of an MRI brain image of a subject is received, and a shrinkage score, which represents the degree of shrinkage of the brain, is calculated based on the MRI brain image. Subsequently, sites to be compared in the brain are identified. Then, a degree of shrinkage, which represents the degree of shrinkage of each of the identified sites, and a shrinkage ratio, which is the ratio between the degrees of shrinkage of the sites, are calculated, and then compared and displayed.

10 Claims, 7 Drawing Sheets

(51) Int. Cl.
  *G06K 9/36* (2006.01)
  *G06K 9/20* (2006.01)
  *A61B 5/055* (2006.01)
  *G16H 50/70* (2018.01)
  *G16H 50/20* (2018.01)

(52) U.S. Cl.
  CPC ............ *G06K 9/2063* (2013.01); *G06K 9/36* (2013.01); *G16H 50/20* (2018.01); *G16H 50/70* (2018.01)

(56) References Cited

FOREIGN PATENT DOCUMENTS

| JP | 2005-237441 A | 9/2005 |
|---|---|---|
| JP | 4 025 823 B2 | 12/2007 |
| JP | 2008-026144 A | 2/2008 |
| JP | 2010-517030 A | 5/2010 |
| JP | 2013-66632 A | 4/2013 |
| JP | 2014-042684 A | 3/2014 |
| WO | 2007/114238 A1 | 10/2007 |
| WO | 2008/093057 A1 | 8/2008 |
| WO | 2011/040473 A1 | 4/2011 |
| WO | 2012/032940 A1 | 3/2012 |

OTHER PUBLICATIONS

Anand, et al. (2009) "Automated Diagnosis of Early Alzheimer's disease using Fuzzy Neural Network." In: Vander Sloten J., Verdonck P., Nyssen M., Haueisen J. (eds) 4th European Conference of the International Federation for Medical and Biological Engineering. IFMBE Proceedings, vol. 22. Springer, Berlin, Heidelberg.*

Alattas et al., "A comparative study of brain vol. changes in Alzheimer's disease using MRI scans," Systems, Applications and Technology Conference (LISAT), 2015 IEEE Long Island.*

Staff et al., Brain vol. And Survival from Age 78 to 85: The Contribution of Alzheimer-Type Magnetic Resonance Imaging Findings, J Am Geriatr Soc. Apr. 2010;58(4):688-95. doi: 10.1111/j.1532-5415.2010.02765.x.*

Dec. 15, 2015 Search Report issued in International Patent Application No. PCT/JP2015/076918.

Dec. 15, 2015 Written Opinion issued in International Patent Application No. PCT/JP2015/076918.

Hiroshi Matsuda, "MRI ni yoru No Yoseki Sokutei", Eizo Joho Medical, 2013.06, vol. 45, No. 6, pp. 505-509, 480-482.

Hiroshi Matsuda, "Neuronuclear imaging in medical examination of dementia", Chiryo to Shindan, 2009, vol. 97, Suppl., pp. 101-111.

Hiroshi Matsuda, "2. Ninchisho no No Gaza Shindan", Geriatric Medicine, 2009, vol. 47, No. 1, pp. 29-33.

Niida et al; "Analysis of the presence or absence of atrophy of the subgenual and subcallosal cingulate cortices using voxel-based morphometry on MRI is useful to select prescriptions for patients with depressive symptoms;" International Journal of General Medicine; Dec. 3, 2014; vol. 4; No. 7; pp. 513-524; XP55465084.

Matsuda et al; "Automatic Voxel-Based Morphometry of Structural MRO by SPM8 plus Diffeomorphic Anatomic Registration Through Exponentiated Lie Algebra Improves the Diagnosis of Probable Alzheimer Disease;" American Journal of Neuroradiology; Jun. 1, 2012; vol. 33; No. 6; pp. 1109-1114; XP55465090.

Matsuda, "Voxel-based Morphometry of Brain MRI in Normal Aging and Alzheimer's Disease;" Aging and Disease; Feb. 2013; vol. 4; No. 1; pp. 29-37; XP55465112.

May 15, 2018 Office Action issued in Japanese Patent Application No. 2014-194786.

Apr. 20, 2018 Search Report issued in European Patent Application No. 15845121.

Jan. 8, 2019 Office Action issued in Japanese Patent Application No. 2014-194786.

* cited by examiner

MEDICAL IMAGE DISPLAY PROCESSING METHOD, MEDICAL IMAGE DISPLAY PROCESSING DEVICE, AND PROGRAM

TECHNICAL FIELD

The present invention relates to a diagnosis support technology, which supports the diagnosis of brain diseases based on brain images taken by MRI etc. In particular, the present invention relates to a technology for providing diagnosis support suitable for cases in which multiple diseases are assumed.

BACKGROUND ART

In recent years, information on the state of the brain is becoming obtainable by nuclear medicine scan such as SPECT (Single Photon Emission Computed Tomography) and PET (Positron Emission Tomography), CT (Computerized Tomography) and MRI (Magnetic Resonance Imaging).

In particular, for the shrinkage of brain tissue, the presence or non-presence of abnormalities can be distinguished by obtaining the volume of particular sites from MRI images and comparing its relative size. For example, according to Patent Document 1, a system for diagnosis support of Alzheimer dementia is disclosed, which provides diagnosis support of Alzheimer dementia by quantitatively evaluating the shrinkage of the middle temporal region using MRI image.

RELATED ART

Patent Documents

Patent Document 1: Japanese Patent No. 4025823
Patent Document 2: JP2013-A-66632

SUMMARY

However, although conventional diagnosis support systems etc. are capable of providing valid diagnostic support information on a specific disease, they have not attained the point of providing valid diagnostic support information that compares diseases when different diseases are simultaneously assumed.

The present invention was made in view of the above-described subjects, and its purpose is to provide a diagnosis support device, which is suitable for comparing different diseases.

In order to accomplish the above-described object, the first invention provides a diagnosis support device, which comprises an identification means, which identifies sites of the brain that are related to multiple diseases from a brain image, and a comparative display means, which calculates and comparatively displays information related to the identified sites. According to the first invention, a diagnosis support device, which is suitable for comparing different diseases, is provided.

It is preferable that the diagnosis support device further comprises a calculation means that calculates a shrinkage score, which represents the degree of shrinkage of the brain, from the brain image, and that the comparative display means displays the identified site along with the shrinkage score distribution on the brain image. Thus, since the shrinkage score distribution is displayed on the brain image along with the sites related to each disease, the shrinkage of the entire brain and the shrinkage of the focused site can be perceived visually.

It is preferable that the comparative display means calculates and displays a degree of shrinkage, which represents the degree of shrinkage in the identified sites, from the shrinkage score. Thus, the shrinkage of the sites related to each disease can be compared quantitatively.

It is preferable that the comparative display means displays the degree of shrinkage for each tissue. Thus, the shrinkage of the sites related to each disease can be compared quantitatively for each tissue.

It is preferable that the comparative display means calculates and displays a shrinkage ratio, which is the ratio between the degrees of shrinkage of each sites. Thus, an index that is effective for identification support, which allows one to uniquely perceive the relationship between different diseases, can be obtained.

It is preferable that the calculation means calculates the shrinkage score by comparing the brain image with the brain image of a healthy subject. Thus, the shrinkage score is calculated by comparison with the brain image of a healthy subject.

It is preferable that the identified sites are sites of the brain in which a difference in shrinkage appears for Alzheimer dementia and dementia with Lewy bodies. Thus, diagnosis support suitable for comparing Alzheimer dementia and dementia with Lewy bodies is realized.

It is preferable that the identified sites are in the vicinity of the middle temporal region and the posterior brain stem. Thus, diagnosis support suitable for comparing Alzheimer dementia and dementia with Lewy bodies is realized.

The second invention provided for achieving the above-described object is a diagnosis support method, which comprises an identification step, wherein sites of the brain that are related to multiple diseases are identified from a brain image, and a comparative display step, wherein information related to the identified sites are calculated and comparatively displayed. According to the second invention, a diagnosis support method, which is suitable for comparing different diseases, is provided.

The third invention provided for achieving the above-described object is a program, which makes a computer function as an identification means, which identifies sites of the brain that are related to multiple diseases from a brain image, and a comparative display means, which calculates and comparatively displays information related to the identified sites. According to the third invention, a program suitable for comparing different diseases is provided.

Effect of the Invention

According to the present invention, a diagnosis support device etc., which is suitable for comparing different diseases, can be provided.

DESCRIPTION OF SOME EMBODIMENTS

Hereinafter, embodiments of the present will be described in detail with reference to the figures.

Figure 1:
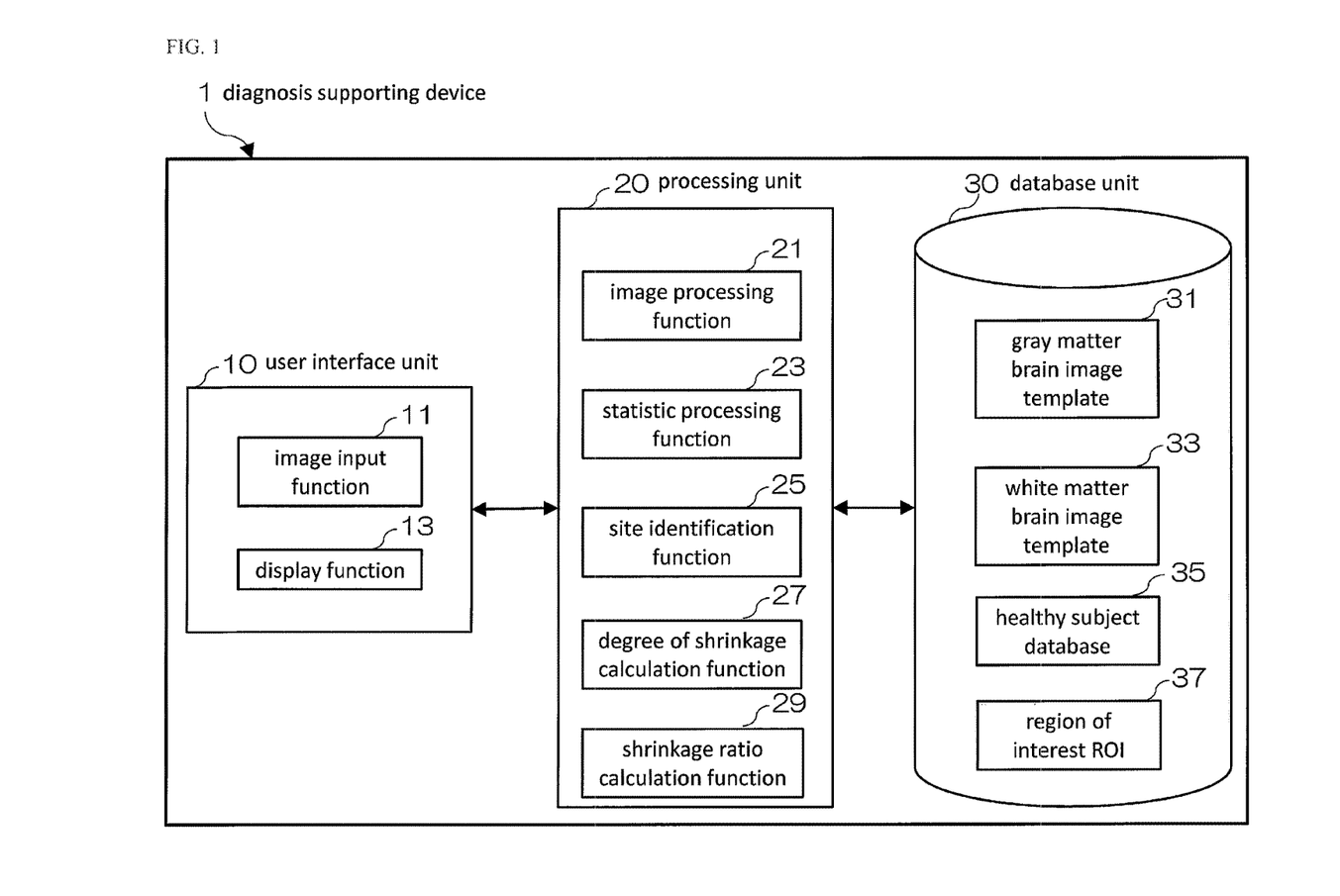
FIG. 1 is a block diagram that describes the function of the diagnosis support device of the present embodiment.

FIG. 1 is a block diagram that describes the function of the diagnosis support device 1. The diagnosis support device 1 comprises a user interface unit 10, a processing unit 20, and a database unit 30.

The user interface unit 10 mainly comprises an image input function 11 that accepts input of MRI image, and a display function 13 that displays the result processed in the processing unit 20.

The processing unit 20 mainly comprises an image processing function 21, which processes the MRI image input from the user interface unit 10, a statistic processing function 23, which calculates indexes such as the Z score etc., and a site identification function 25, which identifies sites (region of interest) specific to each disease that is to be compared, a degree of shrinkage calculation function 27, which calculates the degree of shrinkage, and a shrinkage ratio calculation function 29, which calculates the shrinkage ratio, etc.

Further, in database unit 30, the gray matter brain image template 31, the white matter brain image template 33, the healthy subject image database 35, and the region of interest ROI 37 etc., are stored.

The above gray matter brain image template 31 and white matter brain image template 33 are created for gray matter and white matter separately and stored in the database unit 30 beforehand. Each template may be created and classified according to attribution of the test subject such as age, gender etc.

Note that in the present embodiment, as a technique of anatomical standardization in creating the above-described templates, DARTEL (Diffeomorphic Anatomical Registration Through Exponentiated Lie algebra) is adopted. Since the creation process of templates using DARTEL is the same as that described in Patent Document 1, description will be abbreviated.

[Process of Diagnosis Support Device 1]

Figure 2:
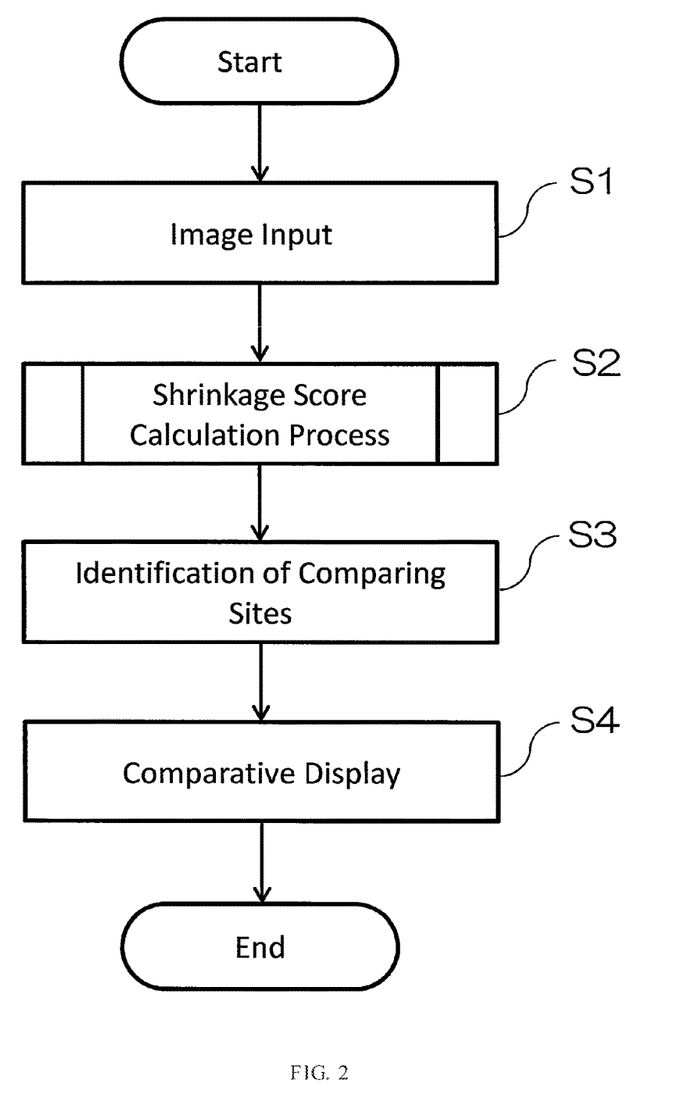
FIG. 2 is a flow chart that describes the processing procedure of the diagnosis support device of the present embodiment.

FIG. 2 is a flow chart that describes the process of the diagnosis support device 1 of the present embodiment. Note that this process is executable by a program in the processing unit 20, which is composed of a computer.

In step S1, the diagnosis support device 1 (image input function 11) accepts the input of the MRI image of the test subject.

In step S2, the diagnosis support device 1 calculates a "shrinkage score", which indicates the degree of shrinkage of the brain, based on the input MRI image of the test subject.

<Shrinkage Score Calculation Process>

Figure 3:
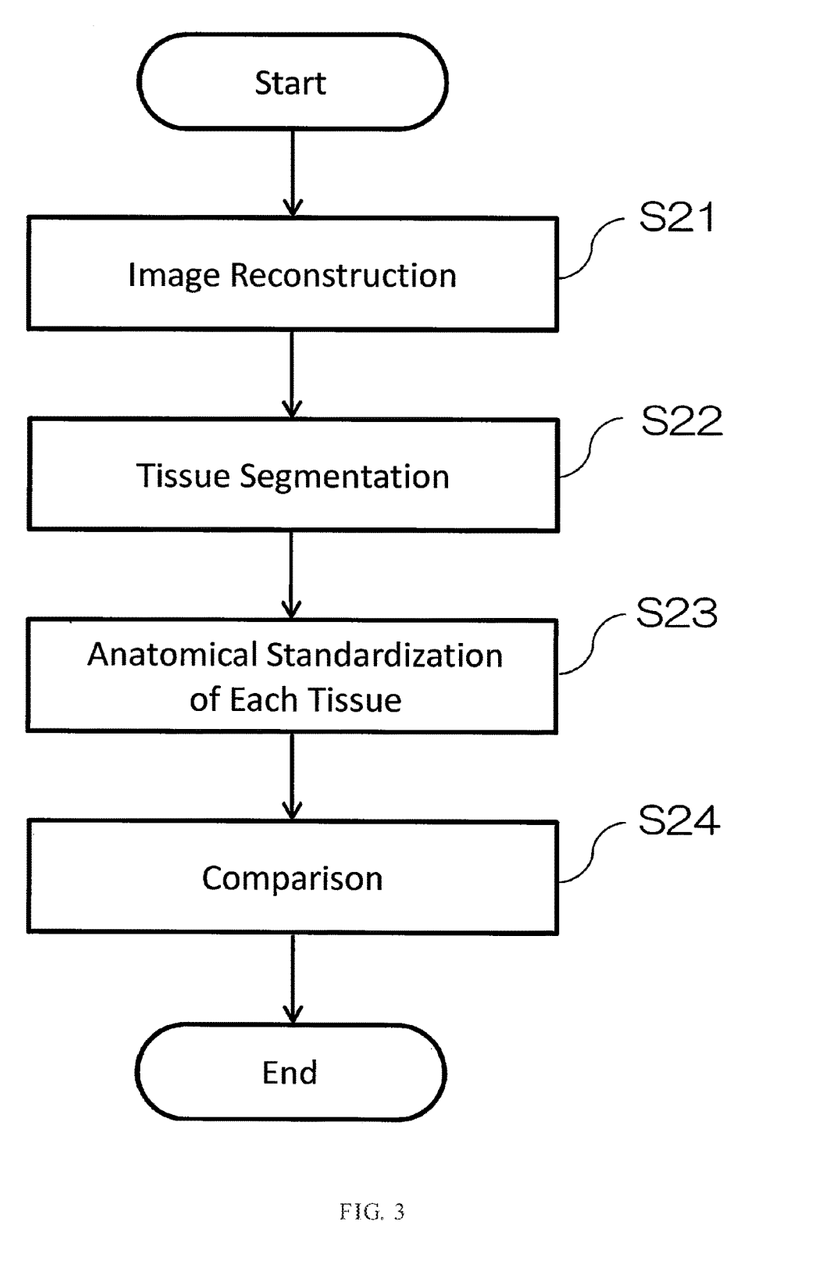
FIG. 3 is a flow chart that describes the calculation procedure for the shrinkage score.

Here, the shrinkage score calculation process in the above-described step S2 will be described with reference to the flow chart of FIG. 3.

(Image Reconstruction)

The diagnosis support device 1 performs "image reconstruction" on the input MRI brain image of the test subject (step S21).

In image reconstruction, first, the MRI brain image of the test subject input is converted to, for example, 100 to 200 T1-emphasized MRI images, which are imaged as slices of arbitrary thickness to include the entire brain. Here, the sliced images are subjected to resampling so that the sides of the voxel in each sliced image are of equal length, beforehand.

The MRI brain image of the test subject, which is subjected to the above treatment, is then subjected to spatial alignment with a standard brain image. Specifically, the MRI brain image of the test subject is subjected to linear transformation (affine transformation), trimming etc., to match the position, angle, size etc. of the standard brain image. This way, the divergence of the position of the test subject's head during MRI imaging etc. can be corrected on the image, thereby enhancing the precision when comparing with standard brain image.

(Tissue Segmentation)

After the image reconstruction of step S21 is performed, the diagnosis support device 1 performs "tissue segmentation" to form a gray matter brain image and a white matter brain image by extracting the gray matter and the white matter (step S22).

Since the above-described T1-emphasized MRI brain image contains white matter, which exhibit high signal value corresponding to the nerve fibers, gray matter, which exhibit medium signal value corresponding to the nerve cells, and cerebral spinal fluid, which exhibit low signal value, an extraction process of the gray matter and the white matter is performed by focusing on the difference in these signal values. Since this process is the same as the process disclosed in Patent Document 1 and Patent Document 2, in which the extraction precision was improved compared to that of Patent Document 1, description will be abbreviated.

(Anatomical Standardization)

Then, the diagnosis support device 1 performs an "anatomical standardization" on the gray matter brain image and the white matter brain image created in step S22 (step S23).

Anatomical standardization is the alignment of the voxel to that of the standard brain image. In the present embodiment, anatomical standardization by DARTEL is performed. Since the process of DARTEL is the same as that of Patent Document 1, description will be abbreviated.

Then, an image smoothing process is performed for the gray matter brain image and the white matter brain image that were subjected to anatomical standardization by DARTEL. By performing such image smoothing, individual differences that did not completely coincide with the anatomical standardization process can be reduced. The specific method of this process is also the same as that described in Patent Document 1.

Further, subsequently, in order to coincide with the voxel value distribution of the image group of healthy subjects for comparison, a concentration value correction for correcting the voxel value of the entire brain is performed.

(Comparison)

In step S24, the diagnosis support device 1 makes a comparison with the MRI image of healthy subjects and calculates a "shrinkage score", which indicates the degree of shrinkage of the brain of the test subject. In the present embodiment, the "Z score", which is a statistical index, is used as the shrinkage score.

Specifically, the gray matter brain image and the white matter brain image of the test subject, which were subjected to anatomical standardization and image smoothing etc. in the above step S23, and the gray matter and white matter MRI brain image group of healthy subjects collected and stored in the healthy subject image database 35 of the database unit 30 beforehand, are statistically compared, and the gray matter and white matter Z scores for the entire voxel or voxels of a specific region in the MRI brain image are calculated as follows. Hereinafter, the Z score for the gray matter will be represented as Z [gray matter] and the Z score for the white matter will be represented as Z [white matter].

[Equation 1]

$$\langle Z \text{ score for gray matter} \rangle$$
$$Z \text{ [gray matter]} = \frac{\mu_1 - x_1}{\sigma_1} \quad (1)$$

$x_1$: voxel value of the gray matter in test subject image
$\mu_1$: average voxel value of the gray matter in healthy subject image group
$\sigma_1$: standard deviation of voxel value of the gray matter in healthy subject image group

[Equation 2]

$$\langle Z \text{ score for white matter} \rangle$$
$$Z[\text{white matter}] = \frac{\mu_2 - x_2}{\sigma_2} \quad (2)$$

$x_2$: voxel value of the gray matter in test subject image
$\mu_2$: average voxel value of the gray matter in healthy subject image group
$\sigma_2$: standard deviation of voxel value of the gray matter in healthy subject image group As shown in the above equation, the Z score is the value obtained by scaling the difference between the voxel value of the test subject image and the corresponding average voxel value of the healthy subject image group by standard deviation, and indicates the relative degree of decrease in the volume of the gray matter and white matter.

Note that the shrinkage score is not limited to the Z score and other indexes that can determine the difference between the voxel value of the test subject image and the healthy subject image may be used as the shrinkage score to indicate the degree of shrinkage (for example, t score etc.).

Further, these gray matter and white matter MRI images of healthy subjects stored in the healthy subject image database 35, which were used in step S24, are created by subjecting each healthy subject image previously collected to processes such as "image reconstruction"→"tissue segmentation"→"anatomical standardization" and image smoothing etc. of step S21 to step S23, sequentially. Note that this process is executable by a program in the processing unit 20, which is composed of a computer.

According to the process described above, the shrinkage score (Z score in the present embodiment) is calculated from the MRI brain image of the test subject.

Returning now to the flow chart of FIG. 2, in step S3, the diagnosis support device 1 identifies sites in the brain (region of interest) specific to each disease being compared. This is mainly realized by the site identification function 25 of the processing unit 20.

For example, the diagnosis support device 1 identifies the region of interest related to each disease based on statistical processing. Specifically, when identifying a region of interest for a certain disease, a 2-sample t-test, which statistically tests the significant difference of two groups in voxel units, is performed for the MRI image group of patients suffering from the disease (patient image group) and the image group of others (non-patient image group). The voxels that show significant difference is considered the voxel characteristic to the disease, and the set of coordinates is identified as the region of interest (ROI).

Further, as described in Japanese Patent No. 5098393, the ROI may be identified using both the level of significance and the rule of thumb.

Furthermore, the ROI may be identified from the patient image (group) only. For example, for the disease image (group), the site in which the degree of shrinkage is larger in correlation to the shrinkage of the entire brain may be identified as the ROI.

Further, the ROI may be identified manually by the personal opinion of the diagnostician.

Hereinafter, in the present embodiment, different diseases, disease A and disease B, are anticipated, and steps are described for the case wherein the region of interest $ROI_A$ for disease A and the region of interest $ROI_B$ for disease B were identified by step S3.

(Comparative Display)

In step S4, the diagnosis support device 1 comparatively displays the diagnostic information etc. for each sites identified in Step S3.

Here, the "degree of shrinkage" and "shrinkage ratio" displayed in step S4 will be described. These indexes are mainly calculated by the degree of shrinkage calculation function 25 and shrinkage ratio calculation function 27 in the processing unit 20.

<Degree of Shrinkage>

The diagnosis support device 1 calculates the "degree of shrinkage", which indicates the degree of shrinkage "in the region of interest". Further, by calculating the degree of shrinkage for each tissue, the gray matter and the white matter, the degree of shrinkage in the sites related to each of the diseases can be quantitatively evaluated for each tissue.

Specifically, the degree of shrinkage of the "gray matter" (Equation 3) and the degree of shrinkage of the "white matter" (Equation 4) in the region of interest $ROI_A$ are calculated as follows from the Z score.

[Equation 3]

$$\langle \text{degree of shrinkage of gray matter in region of interest } ROI_A \rangle ROI_A \text{ degree of shrinkage [gray matter]} = \text{average of positive } Z[\text{gray matter}] \text{ in } ROI_A \quad (3)$$

[Equation 4]

$$\langle \text{degree of shrinkage of white matter in region of interest } ROI_A \rangle ROI_A \text{ degree of shrinkage [white matter]} = \text{average of positive } Z[\text{white matter}] \text{ in } ROI_A \quad (4)$$

Further, the degree of shrinkage of the "gray matter" (Equation 5) and the degree of shrinkage of the "white matter" (Equation 6) in the region of interest $ROI_B$ are calculated as follows.

[Equation 5]

$$\langle \text{degree of shrinkage of gray matter in region of interest } ROI_B \rangle ROI_B \text{ degree of shrinkage [gray matter]} = \text{average of positive } Z[\text{gray matter}] \text{ in } ROI_B \quad (5)$$

[Equation 6]

<degree of shrinkage of white matter in region of interest $ROI_B$>$ROI_B$ degree of shrinkage [white matter]=average of positive Z[white matter] in $ROI_B$ (6)

Note that although in the present embodiment, the "average of the positive Z score" in the region of interest is adopted as the degree of shrinkage, it is not limited to such, and "the average of Z score exceeding a threshold value" or simply "the average Z score" may be adopted. Further, the ratio of voxels with Z values exceeding a threshold value, in relation to the total number of voxels in the ROI, may be adopted, too.

<Shrinkage Ratio>

The diagnosis supporting device 1 further calculates the "shrinkage ratio" based on the above-described degree of shrinkage. Here, the "shrinkage ratio" is an index that represents the largeness of the characteristic of other diseases based on a certain disease, when different diseases are anticipated. The aforementioned degree of shrinkage allows one to perceive the degree of shrinkage for each disease in the region of interest separately, but is not sufficient as an index for identification support of each disease, since it is not an index that allows one to uniquely perceive the relationship of each disease. Thus, in the present embodiment, a "shrinkage ratio", which is the ratio of the degree of shrinkage for each disease as obtained above, is further defined and used as an index for the identification support of each disease.

For example, when disease A and disease B are anticipated, the shrinkage ratio of disease B based on disease A may be calculated as follows.

[Equation 7]

$$\begin{pmatrix} \text{shrinkage ratio of gray matter for} \\ \text{disease } B \text{ based on disease } A \end{pmatrix} \quad (7)$$

$$\text{shrinkage ratio[gray matter]} = \frac{ROI_B \text{ degree of shrinkage[gray matter]}}{ROI_A \text{ degree of shrinkage}}$$

$$\begin{pmatrix} ROI_A \text{ degree of shrinkage} = ROI_A \text{ degree of shrinkage} \\ \text{[gray matter] or } ROI_A \text{ degree of shrinkage [white matter]} \end{pmatrix}$$

[Equation 8]

$$\begin{pmatrix} \text{shrinkage ratio of white matter for} \\ \text{disease } B \text{ based on disease } A \end{pmatrix} \quad (8)$$

$$\text{shrinkage ratio[white matter]} = \frac{ROI_B \text{ degree of shrinkage[white matter]}}{ROI_A \text{ degree of shrinkage}}$$

$$\begin{pmatrix} ROI_A \text{ degree of shrinkage} = ROI_A \text{ degree of shrinkage} \\ \text{[gray matter] or } ROI_A \text{ degree of shrinkage [white matter]} \end{pmatrix}$$

As with the degree of shrinkage, the shrinkage ratio is also calculated for the gray matter and the white matter. Note that for the degree of shrinkage in disease A that is used as the basis (the denominator in the equation), it is preferable to choose the tissue (either "gray matter" or "white matter") in which shrinkage within $ROI_A$ tends to appear stronger in patients of disease A.

By the above equation, when the value of the shrinkage ratio is small, it can be determined that the tendency of disease A is stronger, and when the value of the shrinkage ratio is large, it can be determined that the tendency of disease B is stronger. Thus, the shrinkage ratio may be used as an index to support identification of each disease. For example, by setting an appropriate threshold value, each disease can be identified: when the shrinkage ratios of equations (7) and (8) are smaller than that threshold value, disease A is diagnosed; when the shrinkage ratios are larger than the threshold value, disease B is diagnosed.

Note that although in the present embodiment, the degree of shrinkage and the shrinkage ratio for the gray matter and white matter are calculated separately, the gray matter and white matter may be combined to obtain one degree of shrinkage and shrinkage ratio. This way, the shrinkage of both tissues can be evaluated using one index. This method may become an effective index for situations in which a disease wherein both the gray matter and white matter tissues undergo shrinkage is considered, or a disease wherein it is impossible to determine which tissue, gray matter or white matter, undergoes shrinkage.

However, in such case, a healthy subject image group with the gray matter brain image and the white matter brain image combined has to be prepared in the healthy subject database 35, and by comparing these image groups with the test subject's image in which the gray matter brain image and white matter brain image of the test subject is combined, the Z score is calculated, and using this Z score, the degree of shrinkage and shrinkage ratio are calculated.

For example, the Z score is calculated as follows.

[Equation 9]

⟨Z score for [gray matter + white matter]⟩ (9)

$$Z[\text{gray matter} + \text{white matter}] = \frac{\mu_3 - x_3}{\sigma_3}$$

$x_3$: voxel value of the test subject image with gray matter and white matter combined $\mu_3$: average voxel value of the healthy subject image group with gray matter and white matter combined $\sigma_3$: standard deviation of voxel value of the healthy subject image group with gray matter and white matter combined Further, the degree of shrinkage in the region of interest $ROI_A$ for disease A and the region of interest $ROI_B$ for disease B can be calculated as follows.

[Equation 10]

<degree of shrinkage of [gray matter+white matter] in region of interest $ROI_A$>$ROI_A$ degree of shrinkage [gray matter+white matter]=average of positive Z[gray matter+white matter] in $ROI_A$ (10)

[Equation 11]

<degree of shrinkage of [gray matter+white matter] in region of interest $ROI_B$>$ROI_B$ degree of shrinkage [gray matter+white matter]=average of positive Z[gray matter+white matter] in $ROI_B$ (11)

Further, for example, the shrinkage ratio of disease B based on disease A may be calculated as follows from the above-described degree of shrinkage.

[Equation 12]

$$\langle\text{shrinkage ratio for disease } B \text{ based on disease } A\rangle \quad (12)$$
$$\text{shrinkage ratio[gray matter + white matter]} =$$
$$\frac{ROI_B \text{ degree of shrinkage[gray matter + white matter]}}{ROI_A \text{ degree of shrinkage}}$$

$$\begin{pmatrix} ROI_A \text{ degree of shrinkage} = ROI_A \text{ degree of shrinkage} \\ \text{[gray matter + white matter]}, ROI_A \text{ degree of shrinkage} \\ \text{[gray matter], or } ROI_A \text{ degree of shrinkage [white matter]} \end{pmatrix}$$

Note that for the degree of shrinkage in disease A that is used as the basis (the denominator in the equation), it is preferable to choose the form of tissue (any one of "gray matter and white matter", "gray matter" or "white matter") in which shrinkage within $ROI_A$ tends to appear stronger in patients of disease A.

As described above, various indexes (Z score, degree of shrinkage, shrinkage ratio) are displayed in the user interface unit 10 (display function 13).

Figure 4:
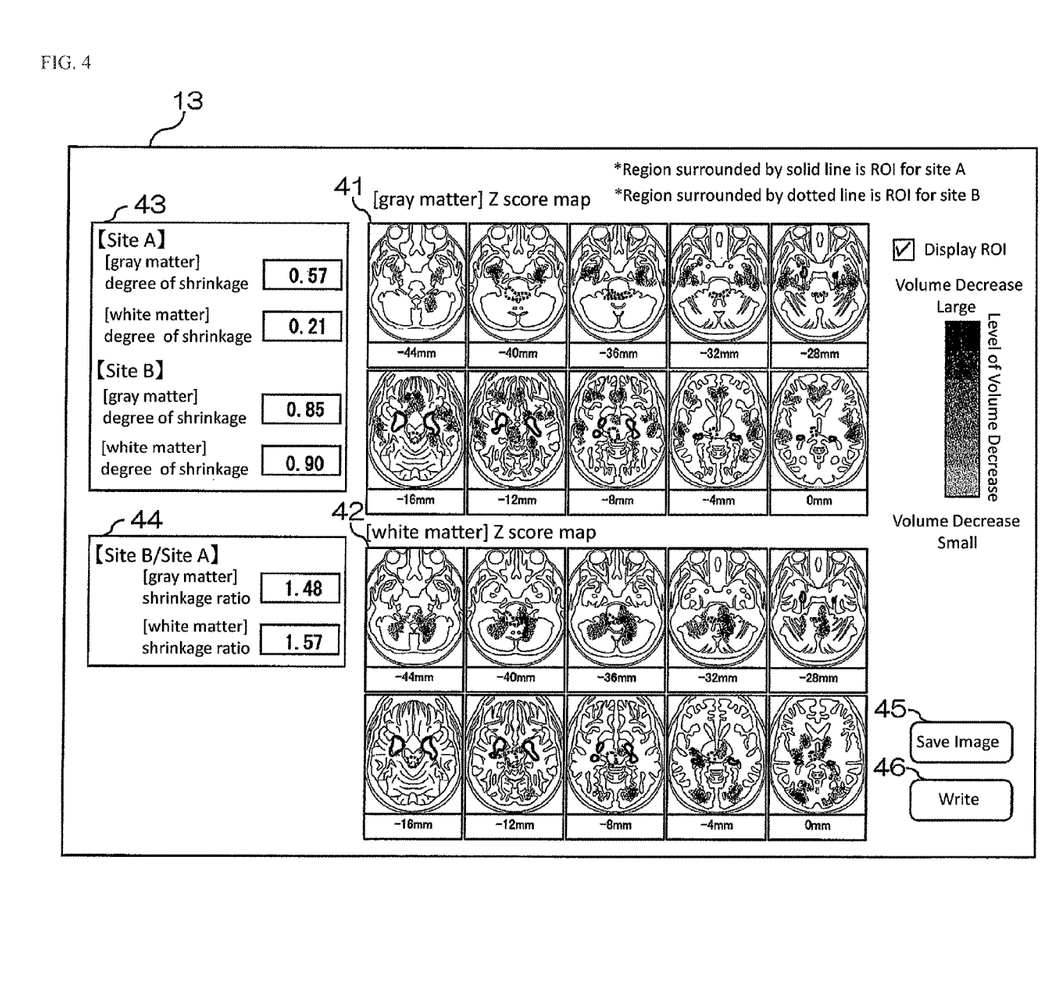
FIG. 4 is a scheme that shows one example of the display of the diagnostic support information etc.

FIG. 4 shows a display example of the user interface unit 10 in the diagnosis supporting device 1.

In the display area 41 in FIG. 4, sliced images of the brain are displayed in line with arbitrary intervals between each. The distribution of the Z score (Z score map) of the "gray matter" (equation 1) is layered and displayed on top of the sliced images. Further, the region of interest for disease A and the region of interest for disease B are displayed.

Figure 5:
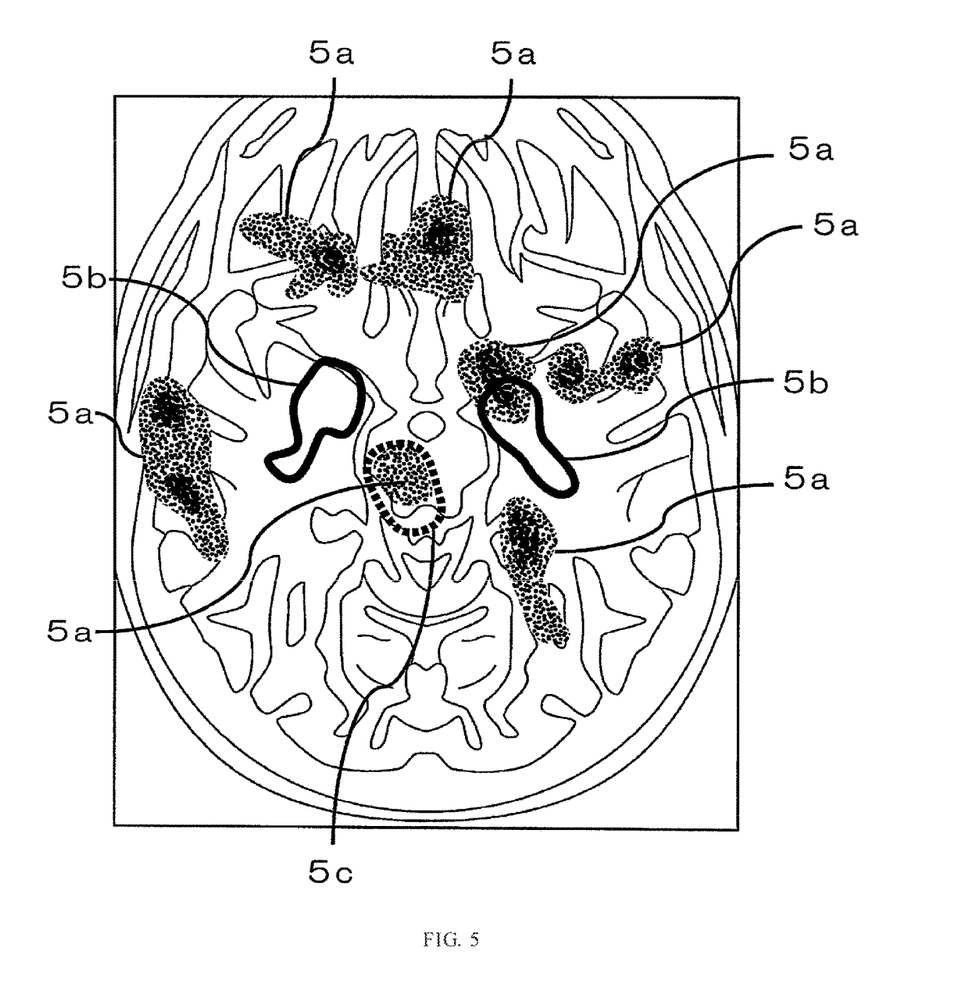
FIG. 5 is a scheme that shows an enlarged slice image.

FIG. 5 shows a magnified sliced image. The Z score map 5a is displayed on the sliced image, and the region of interest for disease A 5b is show in a solid line while the region of interest for disease B 5c is show in a dotted line on the sliced image. Thus, the degree of shrinkage can be perceived for the entire sliced image, while perceiving the degree of shrinkage in the focused sites (regions of interest 5b, 5c) on the sliced image.

In display area 42 of FIG. 4, as with display area 41, sliced images of the brain are displayed in line with arbitrary intervals between each. However, in display are 42, the distribution of the Z score (equation 2) of the "white matter" is layered and displayed on top of the sliced image.

Thus, in display area 41 and 42, by displaying the Z score distribution for each tissue (gray matter, white matter), the difference in shrinkage for each tissue can be perceived.

Note that there are various means of displaying the Z score. For example, it may be displayed in different shades depending on the Z score value, or a contour line may be used for display. Further, the means for displaying the region of interest for each disease may vary. For example, the region of interest may be displayed using different colors for each disease.

In display area 43 of FIG. 4, the degree of shrinkage of the "gray matter" (equation 3) and the degree of shrinkage of the "white matter" (equation 4) in the region of interest for disease A (indicated as site A in FIG. 4) are numerically displayed, and the degree of shrinkage of the "gray matter" (equation 5) and the degree of shrinkage of the "white matter" (equation 6) in the region of interest for disease B (indicated as site B in FIG. 4) are numerically displayed.

Further, in display area 44 of FIG. 4, the shrinkage ratio of the "gray matter" (equation 7) and the shrinkage ratio of the "white matter" (equation 8) for disease B based on disease A are numerically displayed.

As described above, in the present embodiment, the region of interest for each disease is identified by the diagnosis supporting device 1, and each disease is comparatively displayed using various indexes related to the region of interest for the identified disease. Thus, valid diagnostic support information for the comparison or identification support of different diseases is provided to the diagnostician.

EXAMPLE

In the present description, as one example, the possibility of identification support for the two diseases, Alzheimer dementia (hereinafter designated as "AD") and dementia with Lewy bodies (hereinafter designated as "DLB"), was tested.

In AD, since strong shrinkage is observed in the middle temporal region, it is known that identification support can be provided by quantitatively evaluating the shrinkage of the middle temporal region using MRI images.

On the other hand, for DLB, there has been very few evidence reported on disease-specificity in MRI. However, according to recent studies, it has been reported that in DLB, shrinkage appears in the gray matter in the posterior brain stem (dorsal) (Whitwell, Jennifer L. et al. "Focal atrophy in dementia with Lewy bodies on MRI: a distinct pattern from Alzeimer's disease." Brain (2007)). Further, according to another study, it has been reported that in DLB, shrinkage appears in the white matter in the mesencephalon (dorsal part), pons (dorsal) and cerebellum (Nakatsuka, et al. "Discrimination of dementia with Lewy bodies from Alzheimer's disease using voxel-based morphometry of white matter by statistical parametric mapping 8 plus diffeomorphic anatomic registration through exponentiated Lie algebra." Neuroradiology (2013)). According to the findings of such prior studies, it can be speculated that in DLB, there is abnormal tendencies in the vicinity of the posterior brain stem.

In fact, as a result of identifying the abnormal site (site in which shrinkage was large) for AD and DLB using the site identification function 25 of the diagnosis supporting device 1, for AD, the vicinity of the "middle temporal region" appeared as the specific site, while for DLB, the vicinity of the "posterior brain stem" appeared as the specific site. Thus, in the present example, these sites were set as the region of interest for AD and DLB. Here, the region of interest for AD (the vicinity of the middle temporal region) is designated as $ROI_A$, and the region of interest for DLB (the vicinity of the posterior brain stem) is designated as $ROI_B$.

Next, the degree of shrinkage calculated by the degree of shrinkage calculation function 27 of the diagnosis supporting device 1 will be examined. In AD, since, as described above, since the shrinkage of the gray matter in the vicinity of the middle temporal region is large, the degree of shrinkage of the "gray matter" based on equation 3 was adopted. In DLB, according to the above-described prior studies, there is a chance of both the gray matter and white matter in the vicinity of the posterior brain stem being affected, it was decided that evaluation would be made for each tissue. Thus, as the degree of shrinkage for DLB, it was decided that both the degree of shrinkage of the "gray matter" based on equation 5, and the degree of shrinkage of the "white matter" based on equation 6 were to be used.

Then, as the shrinkage ratio calculated by the shrinkage ratio calculation function 29 of the diagnosis supporting device 1, the shrinkage ratio of the gray matter based on equation 7 (hereinafter designated as "τ1") and the shrinkage ratio of the white matter based on equation 8 (hereinafter designated as "τ2") were adopted. Here, for the degree of shrinkage for AD in the region of interest $ROI_A$ (the vicinity of the middle temporal region), which corresponds to the denominator of the shrinkage ratio in equations 7 and 8, the degree of shrinkage of the "gray matter", wherein the tendency of shrinkage appeared to be large in AD patients, was used.

Figure 6:
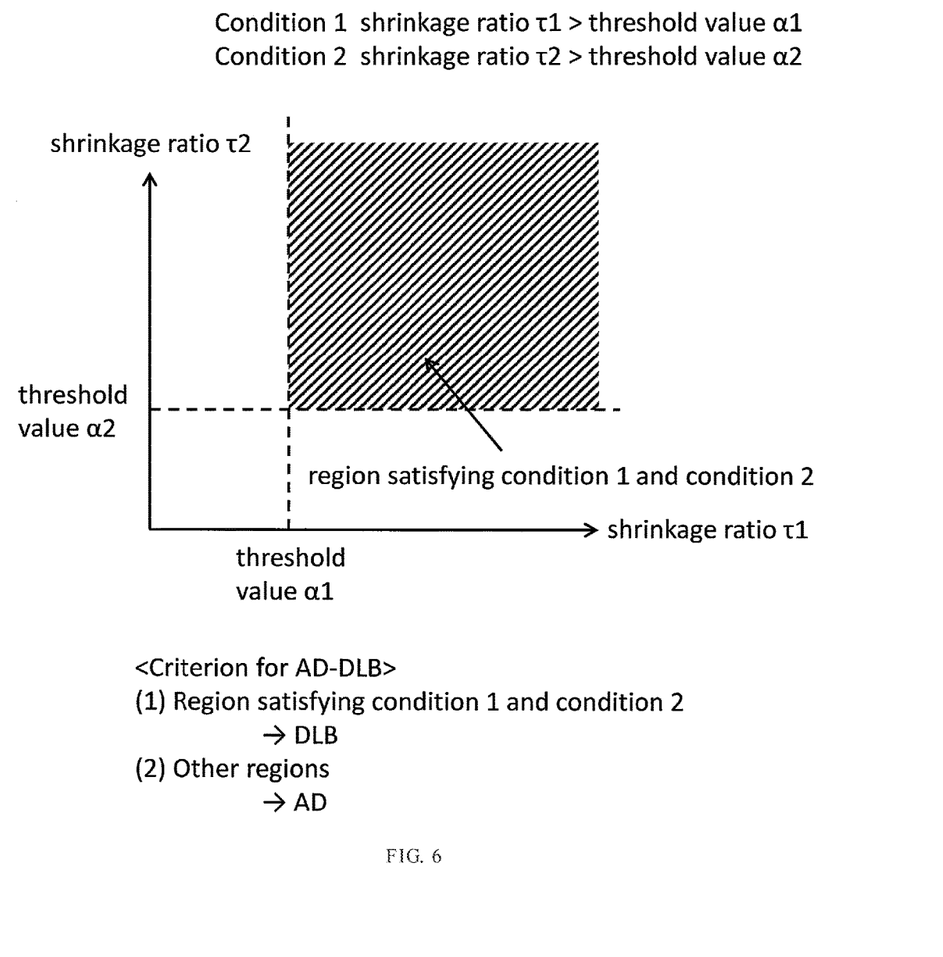
FIG. 6 is a scheme that shows an example of distinguishing diseases by combining the shrinkage ratio for each tissue.

FIG. 6 shows an example of distinguishing AD and DLB by the above-described shrinkage ratio of the gray matter τ1 and the shrinkage ratio of the white matter τ2.

As shown in FIG. 6, threshold value α1 was set for shrinkage ratio τ1 and threshold value α2 was set for shrinkage ratio τ2. When both τ1>α1 and τ2>α2 are satisfied, it can be distinguished that DLB is suspected. In other cases, it can be distinguished that AD is suspected.

Figure 7:
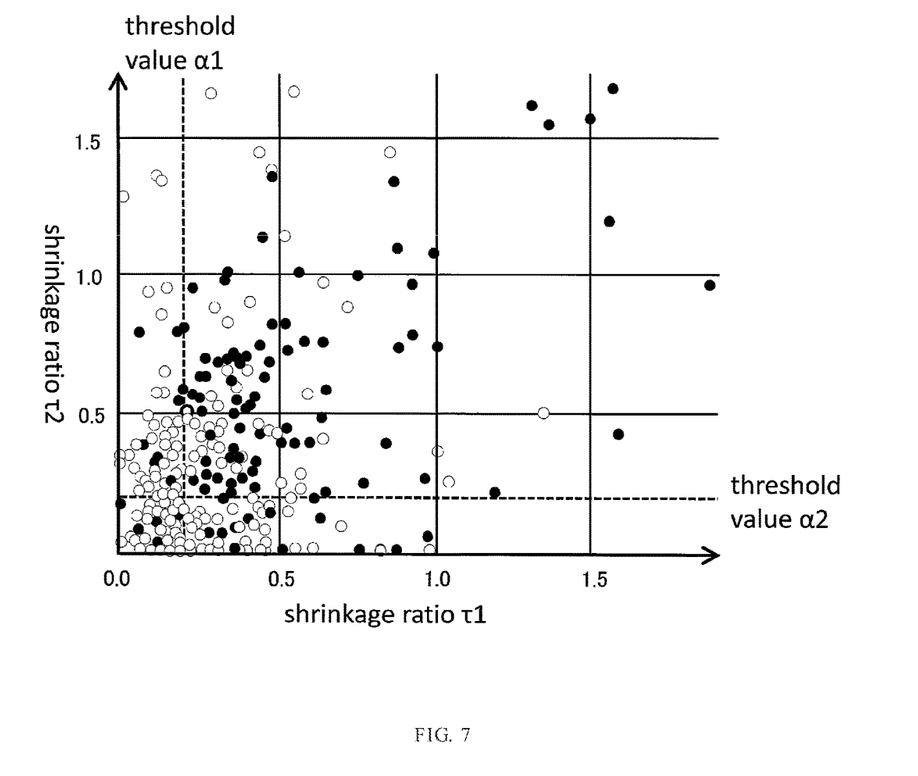
FIG. 7 is a plot diagram of the shrinkage ratio of AD and DLB.

In FIG. 7, shrinkage ratio τ1 and shrinkage ratio τ2 were calculated for patients with AD and patients with DLB using the diagnosis supporting device 1, and the calculated values were plotted. The white dots indicate patients diagnosed with AD, and the black dots indicate patients diagnosed with DLB. In the present embodiment, both threshold values α1 and α2 were set to 0.2.

As shown in FIG. 7, it was found that many DLB patients were distributed in the area that satisfied τ1>α1 and τ2>α2, while AD patients were distributed in other areas, and excellent distinguishing results were obtained. Thus, it was determined that the "shrinkage ratio" was an effective index for identification support targeting AD and DLB.

Although preferred embodiments of the present invention have been described in detail above with reference to the accompanying figures, the present invention is not limited to such examples. It should be obvious to those in the field that examples of various changes and modifications are included within the realm of the technical idea of the present invention, and it should be understood that such examples are included in the technical scope of the present invention.

DESCRIPTION OF NOTATIONS 1 diagnosis supporting device
10 user interface unit
11 image input function
13 display function
20 processing unit
21 image processing function
23 statistic processing function
25 site identification function
27 degree of shrinkage calculation function
29 shrinkage ratio calculation function
30 database unit
31 gray matter brain image template
33 white matter brain image template
35 healthy subject database
37 region of interest ROI

The invention claimed is:

1. A diagnosis support device, which comprises:
a computer that:
receives an MRI image of a brain image of a brain taken by an MRI (Magnetic Resonance Imaging);
identifies sites of the brain that are related to multiple diseases from the brain image, calculates a shrinkage score, which represents a degree of shrinkage of the brain,
calculates information related to the identified sites from the shrinkage score,
calculates the degree of shrinkage, which represents the degree of shrinkage in the identified sites, from the shrinkage score,
calculates a shrinkage ratio, which is the ratio between the degrees of shrinkage of each site; and
comparatively displays the information related to the identified sites from the shrinkage score along with overlaying, over the MRI image, a shrinkage score distribution, so that a person can quantitatively determine different diseases based on the overlaid shrinkage score distribution.

2. The diagnosis support device of claim 1, further comprising
a comparative display that displays the identified site along with the shrinkage score distribution on the brain image.

3. The diagnosis support device of claim 2, wherein the computer calculates the degree of shrinkage or the shrinkage ratio for each tissue.

4. The diagnosis support device of claim 3, wherein the computer calculates the shrinkage score by comparing the brain image with the brain image of a healthy subject.

5. The diagnosis support device of claim 2, wherein the computer calculates the shrinkage score by comparing the brain image with the brain image of a healthy subject.

6. The diagnosis support device of claim 1, wherein the computer calculates the degree of shrinkage or the shrinkage ratio for each tissue of the brain.

7. The diagnosis support device of claim 6, wherein the computer calculates the shrinkage score by comparing the brain image with the brain image of a healthy subject.

8. The diagnosis support device of claim 1, wherein the computer calculates the shrinkage score by comparing the brain image with the brain image of a healthy subject.

9. A diagnosis support method comprising:
receiving an MRI image of a brain image of a brain taken by an MRI (Magnetic Resonance Imaging);
identifying sites of a brain that are related to multiple diseases are identified from a brain image,
calculating a shrinkage score, which represents a degree of shrinkage of the brain, is calculated,
calculating information related to the identified sites from the shrinkage score,
calculating the degree of shrinkage, which represents the degree of shrinkage in the identified sites, from the shrinkage score,
calculating a shrinkage ratio, which is the ratio between the degrees of shrinkage of each site; and
comparatively displays the information related to the identified sites from the shrinkage score along with overlaying, over the MRI image, a shrinkage score distribution, so that a person can quantitatively determine different diseases based on the overlaid shrinkage score distribution.

10. A non-transitory computer readable medium storing a program, which causes a computer to perform a method when executed by a processor, the method comprising:
receiving an MRI image of a brain image of a brain taken by an MRI (Magnetic Resonance Imaging);
identifying sites of the brain that are related to multiple diseases from a brain image,
calculating a shrinkage score, which represents a degree of shrinkage of the brain,
calculating information related to the identified sites from the shrinkage score and comparatively displays it,
calculating the degree of shrinkage, which represents the degree of shrinkage in the identified sites, from the shrinkage score,
calculating a shrinkage ratio, which is the ratio between the degrees of shrinkage of each site; and
comparatively displaying the information related to the identified sites from the shrinkage score along with overlaying, over the MRI image, a shrinkage score distribution, so that a person can quantitatively determine different diseases based on the overlaid shrinkage score distribution.

* * * * *